US010406079B2

(12) United States Patent
Song et al.

(10) Patent No.: US 10,406,079 B2
(45) Date of Patent: Sep. 10, 2019

(54) STRUCTURES CONTAINING THERMO-SENSITIVE GELS

(71) Applicant: KIMBERLY-CLARK WORLDWIDE, INC., Neenah, WI (US)

(72) Inventors: Xuedong Song, Alpharetta, GA (US); Kaiyuan Yang, Cumming, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 15/778,345

(22) PCT Filed: Nov. 30, 2015

(86) PCT No.: PCT/US2015/062924
§ 371 (c)(1),
(2) Date: May 23, 2018

(87) PCT Pub. No.: WO2017/095366
PCT Pub. Date: Jun. 8, 2017

(65) Prior Publication Data
US 2018/0338891 A1 Nov. 29, 2018

(51) Int. Cl.
A61K 8/00 (2006.01)
A61K 8/02 (2006.01)
A61K 8/73 (2006.01)
A61Q 19/00 (2006.01)
A61K 8/81 (2006.01)

(52) U.S. Cl.
CPC ............ A61K 8/0208 (2013.01); A61K 8/731 (2013.01); A61K 8/8129 (2013.01); A61Q 19/00 (2013.01)

(58) Field of Classification Search
None
See application file for complete search history.

(56) References Cited

U.S. PATENT DOCUMENTS

| 2,255,779 | A | 9/1941 | Kent |
| 4,448,704 | A | 5/1984 | Barby |
| 4,837,078 | A | 6/1989 | Harrington |
| 5,685,935 | A | 11/1997 | Heyer |
| 5,840,338 | A | 11/1998 | Roos |
| 5,914,177 | A | 6/1999 | Smith |
| 6,607,636 | B2 | 8/2003 | Ross |
| 6,608,118 | B2 | 8/2003 | Kosaka |
| 6,761,896 | B1 | 7/2004 | Znaiden |
| 6,774,063 | B2 | 8/2004 | Bouchette |
| 7,030,046 | B2 | 4/2006 | Wong |
| 7,381,299 | B2 | 6/2008 | Shannon |
| 7,456,147 | B2 | 11/2008 | Kumar |
| 7,517,582 | B2 | 4/2009 | Amundson |
| 7,670,967 | B2 | 3/2010 | Runge |
| 7,780,979 | B2 | 8/2010 | Hu |
| 8,152,929 | B1 | 4/2012 | Perring |
| 8,603,054 | B2 | 12/2013 | Lemke |
| 8,894,814 | B2 | 11/2014 | Wenzel |
| 8,940,323 | B2 | 1/2015 | Shannon et al. |
| 2002/0060012 | A1 | 5/2002 | Berbner |
| 2003/0175232 | A1 | 9/2003 | Elliott |
| 2004/0081679 | A1 | 4/2004 | Simon |
| 2005/0037079 | A1 | 2/2005 | Son |
| 2005/0136238 | A1 | 6/2005 | Lindsay |
| 2005/0136765 | A1 | 6/2005 | Shannon |
| 2005/0266229 | A1 | 12/2005 | Porticos |
| 2005/0266752 | A1 | 12/2005 | Morin |
| 2006/0005338 | A1 | 1/2006 | Ashe |
| 2006/0246272 | A1 | 11/2006 | Zhang |
| 2007/0088104 | A1 | 4/2007 | Hung |
| 2007/0202315 | A1 | 8/2007 | Duffield |
| 2007/0271719 | A1 | 11/2007 | Schindler |
| 2007/0280974 | A1 | 12/2007 | Son |
| 2009/0084400 | A1 | 4/2009 | Quadbeck-Seeger |
| 2009/0110656 | A1 | 4/2009 | Lemke |
| 2009/0124157 | A1 | 5/2009 | Garza |

(Continued)

FOREIGN PATENT DOCUMENTS

| CN | 101400510 A | 4/2009 |
| CN | 102475513 A | 5/2012 |
| DE | 102005038170 A1 | 2/2007 |
| DE | 202007005648 U1 | 7/2007 |
| DE | 102009010606 A1 | 8/2010 |
| DE | 202008018271 U1 | 9/2012 |
| DE | 102011050786 A1 | 12/2012 |
| FR | 2930435 A1 | 10/2009 |
| JP | 2001310343 A2 | 11/2001 |
| JP | 2005095494 A1 | 2/2008 |
| JP | 4982101 B2 | 7/2012 |
| KR | 101313430 B1 | 10/2013 |
| WO | 05065516 A2 | 7/2005 |
| WO | 09038030 A1 | 3/2009 |
| WO | 13131575 A1 | 9/2013 |

OTHER PUBLICATIONS

Thermoresponsive hydrogels in biomedical applications—a review, Leda Klouda and Antonios Mikos, 2011 Eur J Pharm Biopharm https://www.ncbi.nlm.nih.gov/pmc/articles/PMC3163097/ (Year: 2011).*

Primary Examiner — Jacob T Minskey
(74) Attorney, Agent, or Firm — Kimberly-Clark Worldwide, Inc.

(57) ABSTRACT

The present disclosure is directed to a composite structure that is generally planar in shape. The composite structure has one or more layers; at least one of the layers includes one or more types of fibers. In one aspect, the present disclosure is directed to a composite structure including a hydrophobic support layer and a hydrophilic reservoir layer. The hydrophilic reservoir layer includes a composition that is liquid at temperatures below 30-35 degrees Celsius and that is a hydrogel at temperatures above 30-35 degrees Celsius. In order to better control the phase change of the composition and, therefore, to insulate the hydrophilic reservoir layer from warmth, the hydrophobic support layer may have a thermal conductivity that is 5 to 30 times less, in watts per meter kelvin, than water.

12 Claims, No Drawings

(56) References Cited

U.S. PATENT DOCUMENTS

| | | |
|---|---|---|
| 2009/0160077 A1 | 6/2009 | Aulenta et al. |
| 2009/0199868 A1 | 8/2009 | Cybulski |
| 2010/0264353 A1* | 10/2010 | Hartmann ............... C08B 15/02 |
| | | 252/62 |
| 2010/0286642 A1* | 11/2010 | Allen, Jr. ............... C09J 167/08 |
| | | 604/366 |
| 2011/0088711 A1 | 4/2011 | Bonafos |
| 2011/0117353 A1 | 5/2011 | Henshaw |
| 2011/0123578 A1* | 5/2011 | Wenzel ................ A61K 8/0208 |
| | | 424/401 |
| 2011/0197917 A1 | 8/2011 | Koptis |
| 2011/0217895 A1 | 9/2011 | Peterson |
| 2012/0076972 A1 | 3/2012 | Zhou |
| 2012/0180236 A1 | 7/2012 | Michelson |
| 2013/0029933 A1 | 1/2013 | Schnitzler |
| 2013/0261266 A1 | 10/2013 | Bunyard |
| 2014/0202494 A1 | 7/2014 | Latten et al. |
| 2015/0143647 A1 | 5/2015 | Yang |

* cited by examiner

STRUCTURES CONTAINING THERMO-SENSITIVE GELS

TECHNICAL FIELD

The present disclosure relates to generally two-dimensional structures that include at least two layers. The layers of the structures of the invention may have different properties and perform different functions. The function of each layer of the structure is symbiotic with the functions of the other layers. For example, one layer may be generally hydrophobic and may serve a structural purpose while a second layer is generally hydrophilic and may serve as a reservoir for containing a composition that changes physical states with temperature.

BACKGROUND OF THE DISCLOSURE

Consumer products known as "wipes" can be used for a variety of purposes, including, but not limited to the following: cleaning of the skin (e.g. baby wipes); cleaning of surfaces (e.g. disinfecting wipes and glass-cleaning wipes); application of skin ingredients (e.g. wipes for applying sunscreen). Wipes are generally two-dimensional sheets that are formed from a variety of substrates and that are saturated with a liquid composition formulated to achieve their intended use. When originally conceived, wipes may have been intended to generally mimic paper towels, though wipes tend to be of smaller dimensions. The substrates, or basesheets, used to form wipes products can include fibrous materials, film materials, foam materials or combinations of such materials. The fibrous materials can be selected from cellulose (also known as "pulp") fibers and petroleum-derived polymeric fibers. The basesheet can have a uniform composition of fibers (whether a single type of fiber or a mixture of different types of fibers) or the basesheet can be composed of two or more layers of fibers. Within an individual layer, the fibers can be all of the same type or there can be a mixture of different types of fiber within the individual layer. Between individual layers, there can be similar diversity of fibers and fiber compositions.

Wipes products are typically saturated with an aqueous liquid composition. With proper storage, the wipes will remain wet for long periods of time. However, over time and depending on the integrity of the package holding the wipes, the wetness will change to a "moist" feeling and, eventually, the wipes will dry out. For some uses, the wetness of the wipes is desired to enhance performance of the primary function of the wipes. For example, "baby" wipes that are used during diaper changes for infants and toddlers are wet to aid with removal of bodily waste that may be present on the child's skin as a result of wearing a diaper or other absorbent article. The aqueous composition of the baby wipe is not intended, per se, to transfer to the skin of the child. However, the aqueous composition must be very gentle and non-irritating to skin that can be prone to irritation and rash. In fact, the aqueous compositions used with baby wipes are frequently more than 95% water and may even have 99% water. Another example of the aqueous composition enhancing the primary function of the wipe is with cleaning wipes. The aqueous composition used with cleaning wipes will be formulated to perform the desired cleaning function. Exemplary functions of cleaning wipes include disinfecting, removal of stains and cleaning of special surfaces such as stainless steel and electronics. As with the baby wipes, the aqueous composition of the cleaning wipe is not intended, per se, to transfer to the surface being cleaned.

In other wipes products, it may be desirable to have the aqueous composition actually transfer and be deposited on the surface to which the wipe is coming into contact. For example, wipe/towelette products are sold for the purpose of applying sunscreen and insect repellant. Vitamins, such as Vitamin E, may also be applied to the skin by transfer of a composition from a wipe to the skin. Depending on the formulation of the aqueous composition, users of such wipes products may experience different degrees of success in feeling like the desired composition was sufficiently transferred to the skin. The consequences of unsuccessful transfer of the composition to the skin can cause injury, as in the case of a wipe intended for aiding application of sunscreen. Unfortunately, users of existing wipes products are not consistently confident about the amount of composition transferred to the desired surface; one or more the following could contribute to the lack of confidence: (1) not knowing whether the composition actually transferred to the surface; (2) the wipe feeling dry or insufficiently saturated with the composition to effectuate a transfer; and (3) the desired outcome does not occur (e.g. user experiences a sunburn).

There remains a need for a composite structure, such as a wipe, that is capable of reliably delivering a composition initially present in the wipe to a target surface. There further remains a need for a composite structure that has a sensory cue to assure a user that the composition was, indeed, transferred to the target surface. There is a need for a composite structure that maintains structural integrity while acting as a reservoir for a liquid intended to be transferred to a target surface. Additionally, there remains a need for a composite structure that has a structure of a support layer and a reservoir layer where the reservoir layer holds an aqueous-type composition that is a liquid at temperatures below the intended target surface temperature (e.g. human body temperature) but that changes into a hydrogel when exposed to the temperature of the intended target surface.

SUMMARY OF THE DISCLOSURE

The present disclosure is directed to a composite structure that is generally planar in shape. The composite structure has one or more layers; at least one of the layers includes one or more types of fibers. In one aspect, the present disclosure is directed to a composite structure including a hydrophobic support layer and a hydrophilic reservoir layer. The hydrophilic reservoir layer includes a composition that is liquid at temperatures below 30-35 degrees Celsius and that is a hydrogel at temperatures above 30-35 degrees Celsius. In one aspect, the composition changes phase from a liquid to a hydrogel at human body temperature; average human body temperature is 37 degrees Celsius. The range of 30-35 degrees Celsius is provided to account for some variability in an individual person's actual body temperature and the surrounding environmental conditions. Additionally, the composition of the hydrophilic reservoir layer may be liquid below body temperature (less than 37 degrees Celsius) and a hydrogel at or above body temperature (at or above 37 degrees Celsius).

The hydrophobic support layer may be formed of one or more of urea formaldehyde fibers, polyester resin fibers, epoxy resin fibers, melamine formaldehyde fibers, polycarbonate fibers, silicone particles and cellulose fibers coated with a hydrophobic coating. In order to better control the phase change of the composition and, therefore, to insulate the hydrophilic reservoir layer from warmth, the hydrophobic support layer may have a thermal conductivity that is 5 to 30 times less, in watts per meter kelvin, than water. The hydrophilic reservoir layer may be formed of cellulose fibers. Additionally, the hydrophilic reservoir layer may be formed of 50% or less, by total fiber composition, of thermoplastic fibers. The fibers of the hydrophilic reservoir layer have an absorbent capacity. As a reflection of that absorbent capacity, the hydrophilic reservoir layer may have a ratio of a relative weight of the fibers to the composition of from 1:1 to 1:3.

The composition of the hydrophilic reservoir layer may include a phase change polymer selected from poly(N-isopropylacrylamide); poly(hydroxypropyl methacrylamide); triblock copolymers of polyethylene glycol and poly(hydroxypropyl methacrylamide); triblock copolymers of methyl acrylated poly(N-2-hydroxypropyl) methacrylamide lactate and polyethylene glycol; poloxamers; chitosan and glycerol phosphate disodium; and chitosan-PEG copolymers. The composition may also include one or more of such phase change polymers in addition to other components. For example, the composition may include an active ingredient selected from an antioxidant, a skin moisturizer, Vitamin E and Vitamin C.

The layers of the composite structures of the disclosure, while generally planar, may have different thicknesses. The overall thickness of the composite structure is selected to be appropriate and functional for the desired use of the composite structure. A ratio of a relative thickness of the hydrophobic support layer to the hydrophilic reservoir layer may be from 1:1 to 1:5. The layers are attached or otherwise integrated with each other so as to remain securely together for purposes of performing the desired function of the composite structure. The hydrophobic support layer and the hydrophilic reservoir layer may be laminated together and/or the fibers of the two layers may be entangled together.

DETAILED DESCRIPTION OF THE DISCLOSURE

The present invention relates to composite structures that include a hydrophobic support layer and a hydrophilic reservoir layer. The composite structures are generally planar and may be of a shape that is suitable for the intended function. For example, if the function of the composite structure is to deliver a skin care composition to a user's skin, the composite structure may be rectangular or oval. Each layer of the composite structure will have a thickness. The overall thickness of the composite structure may be selected to be suitable for the intended function of the composite structure. The hydrophilic reservoir layer includes a composition that is liquid at temperatures below 30-35 degrees Celsius and that is a hydrogel at temperatures above 30-35 degrees Celsius. Desirably, the composition changes phase from a liquid to a hydrogel when the hydrophilic reservoir layer comes into contact with a target surface. An example of a target surface may be human skin and therefore, the composition would change phase when put in contact with a temperature of about 37 degrees Celsius. The range of phase change (30-35 degrees Celsius) is adjusted for environmental conditions in close proximity to the target surface. The hydrophobic support layer acts as a thermal insulating layer to prevent premature phase change of the composition.

The Hydrophilic Reservoir Layer

The hydrophilic reservoir layer of the composite structures of the invention may be formed entirely of cellulose-based fibers because of their hydrophilic nature and the capacity of such fibers to hold a fluid. For example, a sheet or sponge-like layer of cellulose fibers can hold a fluid because of the absorbent capacity of cellulose. While the hydrophilic reservoir layer of the present invention may be composed entirely of cellulose-based fibers, the hydrophilic reservoir layer may also include non-cellulose-based fibers—including fibers typically used to form nonwoven materials. The fibers typically used to form nonwoven materials are made from thermoplastic polymers. Fiber materials are selected so that the layer remains hydrophilic and capable of "holding" a composition. Typically, the percentage of fibers formed from a thermoplastic polymer will be 50% or less of the total fiber composition of the hydrophilic reservoir layer.

A variety of thermoplastic polymer fibers may be used to form part of the fiber composition of the hydrophilic reservoir layer. The polymer fibers may be formed using a variety of nonwoven fiber-forming techniques including, but not limited to, spunbond, meltblown, coform, air-laid, bonded-carded web materials, hydroentangled (spunlace) materials and combinations of these techniques. These techniques are well-known for forming nonwoven materials composed of fibers. The fibers forming these nonwoven materials can be produced by meltblowing or spunbonding processes, including those producing bicomponent, biconstituent or polymer blend fibers that are well known in the art. These processes generally use an extruder to supply melted thermoplastic polymer to a spinneret where the polymer is fiberized to yield fibers that can be staple length or longer. The fibers are then drawn, usually pneumatically, and deposited on a moving formations mat or belt to form a nonwoven fabric. The fibers produced in the spunbond and meltblown processes can be microfibers. Microfibers of the present disclosure are small diameter fibers having an average diameter not greater than about 75 microns, for example, having an average diameter of from about 0.5 microns to about 50 microns, or more particularly, microfibers can have an average diameter of from about 2 microns to about 40 microns. As is contemplated for the hydrophilic reservoir layer component of the present invention, nonwoven fabrics can be a combination of thermoplastic fibers and natural fibers, such as, for example, cellulosic fibers (softwood pulp, hardwood pulp, thermomechanical pulp, etc.).

In addition to nonwoven materials, the hydrophilic reservoir layer of the composite structures of the invention can also be made of woven fabric, knit fabric or combinations of these and other materials. The hydrophilic reservoir layer can also be made of paper tissue or paper towel, as will be described herein.

The hydrophilic reservoir layer may be formed from a spunbond web containing monocomponent and/or multi-component fibers. Multicomponent fibers are fibers that have been formed from at least two polymer components. Such fibers are usually extruded from separate extruders but spun together to form one fiber. The polymers of the respective components are usually different from each other although multicomponent fibers can include separate components of similar or identical polymeric materials. The individual components are typically arranged in substantially constantly positioned distinct zones across the cross-section of the fiber and extend substantially along the entire length of the fiber. The configuration of such fibers can be, for example, a side-by-side arrangement, a pie arrangement, or any other arrangement.

When used, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al.

The hydrophilic reservoir layer may also be a coform material. The term "coform material" generally refers to composite materials including a mixture or stabilized matrix of thermoplastic fibers and a second non-thermoplastic material. As an example, coform materials can be made by a process in which at least one meltblown die head is arranged near a chute through which other materials are added to the web while it is forming. Such other materials can include, but are not limited to, fibrous organic materials such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al. For the hydrophilic reservoir layers of the invention, it is desirable for the coform material to include 50% or more of cellulose-based fibers.

In another aspect, the hydrophilic reservoir layer may be a hydroentangled nonwoven fabric. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al.

Hydroentangled nonwoven webs with staple fibers entangled with thermoplastic fibers are suitable for use as the hydrophilic reservoir layer for the composite structures of the invention. In one example of a hydroentangled nonwoven web, the staple fibers are hydraulically entangled with substantially continuous thermoplastic fibers. The staple fibers can be cellulosic staple fibers, non-cellulosic stable fibers or a mixture thereof. Suitable non-cellulosic staple fibers includes thermoplastic staple fibers, such as polyolefin staple fibers, polyester staple fibers, nylon staple fibers, polyvinyl acetate staple fibers, and the like or mixtures thereof. Suitable cellulosic staple fibers include for example, pulp, thermomechanical pulp, synthetic cellulosic fibers, modified cellulosic fibers, and the like. Cellulosic fibers can be obtained from secondary or recycled sources. Some examples of suitable cellulosic fiber sources include virgin wood fibers, such as thermomechanical, bleached and unbleached softwood and hardwood pulps. Secondary or recycled cellulosic fibers can be obtained from office waste, newsprint, brown paper stock, paperboard scrap, etc., can also be used. Further, vegetable fibers, such as abaca, flax, milkweed, cotton, modified cotton, cotton linters, can also be used as the cellulosic fibers. In addition, synthetic cellulosic fibers such as, for example, rayon and viscose rayon can be used. Modified cellulosic fibers are generally composed of derivatives of cellulose formed by substitution of appropriate radicals (e.g., carboxyl, alkyl, acetate, nitrate, etc.) for hydroxyl groups along the carbon chain.

A suitable hydroentangled nonwoven web is a nonwoven web composite of polypropylene spunbond fibers, which are substantially continuous fibers, having pulp fibers hydraulically entangled with the spunbond fibers. Another particularly suitable hydroentangled nonwoven web is a nonwoven web composite of polypropylene spunbond fibers having a mixture of cellulosic and non-cellulosic staple fibers hydraulically entangled with the spunbond fibers. For the hydrophilic reservoir layers of the invention, it is desirable for the hydroentangled material to include 50% or more of cellulose-based fibers.

The thermoplastic fibers that may be used to form part of the hydrophilic reservoir layer may be formed from any thermoplastic polymer. Exemplary thermoplastic polymers include polyolefins, polyesters, polyamides, polyurethanes, polyvinylchloride, polytetrafluoroethylene, polystyrene, polyethylene terephthalate, biodegradable polymers such as polylactic acid, and copolymers and blends thereof. Suitable polyolefins include polyethylene, e.g., high density polyethylene, medium density polyethylene, low density polyethylene and linear low density polyethylene; polypropylene, e.g., isotactic polypropylene, syndiotactic polypropylene, blends of isotactic polypropylene and atactic polypropylene, and blends thereof; polybutylene, e.g., poly(l-butene) and poly(2-butene); polypentene, e.g., poly(1-pentene) and poly (2-pentene); poly(3-methyl-1-pentene); poly(4-methyl 1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include polyethylene terephthalate, polytrimethylene terephthalate, polybutylene terephthalate, polytetramethylene terephthalate, polycyclohexylene-1,4-dimethylene terephthalate, and isophthalate copolymers thereof, as well as blends thereof. These thermoplastic polymers can be used to prepare both substantially continuous fibers and staple fibers.

The hydrophilic reservoir layer may also be a tissue product. The tissue product may be of a homogenous or multi-layered construction, and tissue products made therefrom can be of a single-ply or multi-ply construction. The tissue product may have a basis weight of about 10 $g/m^2$ to about 65 $g/m^2$ and a density of about 0.6 g/cc or less. In other aspects, the basis weight can be about 40 $g/m^2$ or less and the density can be about 0.3 g/cc or less. In still other aspects, the density can be about 0.04 g/cc to about 0.2 g/cc. Unless otherwise specified, all amounts and weights relative to the paper are on a dry basis. Tensile strengths in the machine direction can be in the range of from about 100 to about 5,000 grams per inch of width. Tensile strengths in the cross-machine direction are from about 50 grams to about 2,500 grams per inch of width. Absorbency is typically from about 5 grams of water per gram of fiber to about 9 grams of water per gram of fiber.

Conventionally pressed tissue and paper products and methods for making such products are well known in the art. Where appropriate, tissue and paper products are typically made by depositing a papermaking furnish on a foraminous forming wire, often referred to in the art as a forming wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided from a pressurized headbox, which has an opening for delivering a thin deposit of pulp furnish onto the former wire to form a wet web. The web is then typically dewatered to a fiber consistency of from about 7% to about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The formed sheets are considered to be compacted since the entire web is subjected to substantial mechanical compressional forces while the fibers are moist and are then dried while in a compressed state. In other aspects, the tissue or paper can be formed by creping as is known in the art.

An uncreped through-air-drying technique may be used to form the tissue product used as the hydrophilic reservoir layer in the composite structures of the invention. Through-air-drying can increase the bulk and softness of the web. Examples of such a technique are disclosed in U.S. Pat. No. 5,048,589 to Cook, et al.; U.S. Pat. No. 5,399,412 to Sudall, et al.; U.S. Pat. No. 5,510,001 to Hermans, et al.; U.S. Pat. No. 5,591,309 to Ruqowski, et al.; U.S. Pat. No. 6,017,417 to Wendt, et al., and U.S. Pat. No. 6,432,270 to Liu, et al. Uncreped through-air-drying generally involves the steps of: (1) forming a furnish of cellulosic fibers, water, and optionally, other additives; (2) depositing the furnish on a traveling foraminous belt, thereby forming a fibrous web on top of the traveling foraminous belt; (3) subjecting the fibrous web to through-air-drying to remove the water from the fibrous web; and (4) removing the dried fibrous web from the traveling foraminous belt.

When the hydrophilic reservoir layers is formed from a nonwoven material, the nonwoven material may be a multilayer laminate. An example of a multilayer laminate is where some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al., and U.S. Pat. No. 4,374,888 to Bornslaeger. Such a laminate can be made by sequentially depositing onto a moving forming belt first a spunbond fabric layer, then a meltblown fabric layer and last another spunbond layer and then bonding the laminate. Alternatively, the fabric layers can be made individually, collected in rolls, and combined in a separate bonding step. Such fabrics usually have a basis weight of from about 0.1 to 12 OSY (ounces per square yard) (6 to 400 grams per square meter), or more particularly from about 0.75 to about 3 OSY. The laminate may be thermally (e.g., pattern bonded, through-air dried), ultrasonically, adhesively and/or mechanically (e.g. needled) bonded. For instance, various pattern bonding techniques are described in U.S. Pat. No. 3,855,046 to Hansen; U.S. Pat. No. 5,620,779 to Levy, et al.; U.S. Pat. No. 5,962,112 to Haynes, et al.; U.S. Pat. No. 6,093,665 to Sayovitz, et al.; U.S. Design Pat. No. 428,267 to Romano, et al.; and U.S. Design Pat. No. 390,708 to Brown. The laminate may be bonded by continuous seams or patterns. As additional examples, the laminate may be bonded along the periphery of the sheet or simply across the width or cross-direction of the web adjacent the edges. Other bonding techniques, such as a combination of thermal bonding and latex impregnation, can also be used. Alternatively and/or additionally, a resin, latex or adhesive can be applied to the laminate by, for example, spraying or printing, and dried to provide the desired bonding. Still other suitable bonding techniques can be described in U.S. Pat. No. 5,284,703 to Everhart, et al., U.S. Pat. No. 6,103,061 to Anderson, et al., and U.S. Pat. No. 6,197,404 to Varona.

The Hydrophobic Support Layer

The hydrophobic support layer may be formed of hydrophobic fibers or of a water-impermeable substrate or film. Desirably, the hydrophobic support layer has a low thermal conductivity to slow the transfer of heat through the hydrophobic support layer to the hydrophilic reservoir layer. The purpose of slowing heat transfer is to prevent premature formation of the gel form of the composition in the hydrophilic reservoir layer. Desirably, the hydrophobic support layer has a thermal conductivity that is 5 to 30 times less, in watts per meter kelvin, than water. Even more desirably, the hydrophobic support layer has a thermal conductivity that is 10 to 30 times less, in watts per meter kelvin, than water. The thermal conductivity of water is 0.58 watts per meter kelvin. When the hydrophobic support layer is formed of hydrophobic fibers, it may be formed of fibers made from thermal-setting polymers.

Examples of polymers that may be used to form the hydrophobic support layer of the invention include but are not limited to those listed in Table 1.

TABLE 1

| Thermal-Setting Polymers | | |
|---|---|---|
| Name | Properties | Applications and Uses |
| Urea formaldehyde | Strong, insulator, brittle, hard, stiff. | Electrical fittings, handles and knobs |
| Polyester resin | Liquid raw state, stiff hard, insulator, chemical resistance, brittle without fibre reinforcement. | Casting, bonding fibres (glass, Kevlar, carbon fibre) |
| Epoxy resins trade names include Araldite. | Good insulator, brittle chemical resistant. | Adhesives, bonding fibres, encapsulation. |
| Melamine formaldehyde | Hard, strong, heat resistant. | Adhesives, bonding fibres, encapsulation. |
| Polycarbonate | Hard, strong, transparent, high refractive index | Spectacle lenses |

Thermal-setting melamine fibers suitable for the hydrophobic support layer of the composite structures of the invention may either be continuous or staple fibers, such as the meltblown fibers described in U.S. Patent Application Publication No. 2009/0084400 to Quadbeck-Seeger, short-cut dry staple fibers from Basofil Inc., and short-cut wet staple fibers from Engineered Fiber Technology. The thermal conductivity of melamine fibers is about 0.03 watts per meter kelvin.

In addition to thermal-setting fibers, the hydrophobic support layer may also include cellulose-based fibers that have been treated with a hydrophobic coating such as a fluorosurfactant or fluoroadditive. For example, a spray coating system could be used to form the hydrophobic support layer on one surface of a wipe material formed of a coform material, a HYDROKNIT material or paper towel. A suitable spray system is an atomized Model 1550+ Autojet Modular Spray System available from Spraying Systems Co. The modular spray system may be attached to a hydraulic pressure spray box and a through air dryer (TAD). A suitable hydrophobic coating solution may include CAPSTONE ST-100 fluorosurfactant available from The Chemours Company or ZONYL fluoroadditive also available from The Chemours Company.

The thermal-setting fiber hydrophobic support layer preferably includes at least 70% or greater thermal-setting fibers by weight (i.e., binder fibers, binder coatings, and other added fibers should not exceed 30%). The thermal-setting fiber hydrophobic support layer can be as low as ~3-10 GSM (grams per square meter) to as high as ~30 GSM regardless of the basis weight of the hydrophilic reservoir layer. The thermal-setting fibers should be fixed to reduce or eliminate their movement during use of the composite structure. Fixing the fibers increases friction between fibers and the hydrophilic reservoir layer. A rigid fixation mechanism may be incorporated into a hydrophobic support layer made with thermal-setting fibers to ensure maximum friction between fibers and the hydrophilic reservoir layer. The rigid fixation mechanism can be additional polymer resin sprayed on the fibers to fix them together. Preferably, the fiber fixation materials are also selected from thermal-setting polymers to both fix the fibers and to prevent the fixation mechanism itself from moving during use of the composite structure.

Suitable fixing materials include the following: various Bi—Co binder fibers such as CoPET/PET T-201, T-203 from Fiber Innovation Technologies, various binder polyvinyl alcohols (PVA) fibers such as those from Engineered Fiber Technology, various latex polymers such as those from Celanese Emulsion Polymers, HYCAR and PERMAX brand emulsions from Lubrizol, emulsion polymers from Kraton, and, most preferably, the thermal-setting polymers such as melamine resins such as CYMEL 328 and CYMEL 385 resins from CYTEC, Inc.

Thermal-setting fibers suitable for the hydrophobic support layer of the present invention can be in various lengths and shapes. In some aspects, fibers can have movement fixation mechanisms between fibers before any further fixation treatment is applied. One example of such fibers is documented in U.S. Patent Application Publication No. 2010/0269318 to Panzer, et al., in which fibers have self-connecting branching points. A branching point is a point at which two or more fibers continuing in their respective longitudinal directions converge in one point and are physically connected to each other by merging. Fibers with such branching points are advantageous as they provide an already built-in fiber fixation mechanism. At the same time, such branching points can help to hold brittle thermal-setting fibers together for preventing or at least reducing fiber linting during use.

Combination of the Hydrophobic Support Layer and the Hydrophilic Reservoir Layer The layers may be laminated to each other either mechanically or chemically entangled with each other (if both include fiber components). One layer of a hydrophilic material may also be treated with a hydrophobic coating as described herein so that the material functions as both the hydrophobic support layer and the hydrophilic reservoir layer.

Meltblown thermal-setting melamine fibers and staple fibers can both be attached to other materials, such as the hydrophilic reservoir layer, by laminating pre-made fiber webs with desired thicknesses and basis weights. Alternatively, meltblown webs or staple fiber webs can be formed directly onto pre-made or in-situ-made hydrophilic reservoir layers in a continuous process. For example, a thermal-setting melamine staple fiber hydrophobic support layer can be formed onto an in-situ-formed pulp fiber web by introducing staple melamine fibers and pulp fibers from layered head boxes in a traditional paper-making process. In this example, pulp fiber web is introduced from a bottom headbox to form the pulp-fiber-rich hydrophilic reservoir layer. Melamine fibers are then deposited from the top head box to the already-formed capture substrate. In this in-situ two-layer-forming example, the top melamine fiber layer can be as low as 3 GSM (grams per square meter) to as high as desired. More specifically, a hydrophobic support layer of melamine fibers (BASOFIL fibers having a cutting length of about 5-10 millimeters) having a basis weight of from 3 to 30 GSM (grams per square meter) may be produced on top of a pulp fiber layer having a basis weight of from 30 to 60 GSM using a wet-laid paper-making process. The pulp fibers may be HP-11 fibers available from Buckeye Technologies, Inc.

In another example of the present invention, the composite structure may be formed of a hydrophobic support layer attached to a mixed hydrophobicity material that is capable of functioning as a hydrophilic reservoir layer capable of holding a composition. A more specific example of such a mixed hydrophobicity material would be a coform material that is more hydrophobic on one or both outer surfaces and hydrophilic on the other surface (if one surface is more hydrophobic) or hydrophilic in the middle (if both surfaces are more hydrophobic). The more hydrophobic surface may have a thermal conductivity closer to that of water (than the thermal conductivity of the hydrophobic support layer). For example, high density polyethylene has a thermal conductivity of 0.45 to 0.51 watts per meter kelvin and polypropylene has a thermal conductivity of 0.11 to 0.22 watts per meter kelvin.

In a further example of the present invention, the composite structure may be formed from a pre-made hydrophobic layer that is attached onto a regular nonwoven layer or a paper towel layer by lamination or other adhesion technique. The pre-made hydrophobic support layer may be made of a meltblown melamine fiber web (~10-60 grams per square meter, available from Borealis, Inc.). The hydrophilic reservoir layer may be one or more of coform, HYDROKNIT material, VIVA paper towel and SCOTT paper towel. The adhesive for laminating the two layers together may be selected from suitable commercial sources including SUPER 77 multipurpose spray adhesive from 3M.

Each of the hydrophobic support layer and the hydrophilic reservoir layer has a thickness. The layers may have the same or different thicknesses. Generally speaking, the thickness of the hydrophilic reservoir layer may be greater than the thickness of the hydrophobic support layer because of the storage of the composition. For example, the relative thicknesses of the two layers may be represented as a ratio. The ratio of the relative thickness of the hydrophobic support layer to the hydrophilic reservoir layer is from 1:1 to 1:5. Therefore, the thickness of the hydrophilic reservoir layer may be up to five times greater than the thickness of the hydrophobic support layer. Along these lines- and consistent with the functional purpose of the hydrophilic reservoir layer—the relative weight distribution within the hydrophilic reservoir layer between the fibers and the composition is weighted toward the composition. For example, a ratio of the relative weight of the fibers to the composition may be from 1:1 to 1:3. Consequently, the weight of the composition in the hydrophilic reservoir layer may be three times greater than the weight of the fibers.

The Composition of the Invention

The hydrophilic reservoir layer includes a composition. The composition includes a polymer that is water soluble and in a liquid state at a temperature of 30 degrees Celsius and forms a hydrogel at a temperature of 33 degrees Celsius or higher. In addition to including a polymer that changes phase (from liquid to hydrogel) at body temperature (average is 37 degrees Celsius) or in close proximity to body temperature, the entire composition "stored" in the hydrophilic reservoir layer changes phase at body temperature. Desirably, the phase change occurs rapidly when body temperature is reached or in close proximity. The phase change should occur within ten minutes and desirably the phase change occurs in less than a minute. Even more desirably, the phase change occurs in ten seconds or less. The phase change of the composition is reversible.

Examples of suitable polymers for use in the composition include poly(N-isopropylacrylamide); poly(hydroxypropyl methacrylamide); triblock copolymers of polyethylene glycol and poly(hydroxypropyl methacrylamide); triblock copolymers of methyl acrylated poly(N-2-hydroxypropyl) methacrylamide lactate and polyethylene glycol; poloxamers; chitosan and glycerol phosphate disodium; and chitosan-PEG copolymers. In addition to the phase-changing polymer, the compositions may include "active" skin care ingredients. The "active" ingredients may include ingredients known for providing skin care benefits, wound care benefits, moisturizing benefits, preservative benefits, prebiotic and probiotic benefits. More specifically, suitable active ingredients may include one or more of antioxidants, moisturizers, Vitamin E and Vitamin C. The active ingredients may be incorporated into the compositions in a variety of forms including controlled-release forms such as particles. The compositions may also include pre-moisturizing solvents such as water and water-containing solvents to provide a pre-moisturized form. Alternatively, the compositions may not include a pre-moisturizing solvent and may be present in the hydrophilic reservoir layer in a dry form.

Desirably, the composition is formulated so that when the composite structure is wiped across a user's skin, the composition is transferred to the skin. Additionally, when the composition that is transferred to the skin comes into contact with the skin at a temperature greater than 33 degrees Celsius, the composition changes phase from a liquid to a hydrogel. The formation of a hydrogel will form a thin and relatively uniform layer of the composition on the skin. If the composition contains an active ingredient, the active ingredient will be provided to the skin in a relatively uniform manner. When the composition changes phase, the transfer of the composition from the hydrophilic reservoir layer to the skin or another surface (at a temperature greater than 33 deg. Celsius) is substantially one-way and the composition does not move back onto the hydrophilic reservoir layer. The more wipes across the target surface, such as the skin, the greater the quantity of composition that will be transferred. If the hydrophilic reservoir layer of the composite structure is "dry", the hydrophilic reservoir layer will need to be moistened or otherwise exposed to water or a water-containing solvent prior to use of the composite structure.

An example of a suitable phase change polymer for use in the compositions of the invention is EXPERTGEL 230 thermoreversible polymer and EXPERTGEL 56 thermoreversible polymer both available from Polymer Expert, Pessac, France. When either of these polymers is mixed with water to form a 5% aqueous solution, they are transparent and water-like at room temperature. When the 5% aqueous solution is applied to the skin, the solution changes phase to form a thin layer of transparent hydrogel.

Examples of the Present Invention

In a first experiment, a composite structure was formed of a hydrophobic support layer and a hydrophilic reservoir layer. The hydrophobic support layer was formed of melamine fibers and the hydrophilic reservoir layer was formed of pulp fiber. The two-layered composite structure was formed using a standard paper manufacturing process as described herein. The composite structure was cut into three (3) samples each having dimensions of 2 inches by 2 inches. With regard to the first sample, the hydrophilic reservoir layer was loaded with 500 microliters of water including 0.4 milligrams/milliliters of a Food, Drug & Cosmetic blue dye. With regard to the second sample, the hydrophilic reservoir layer was loaded with 500 microliters of a 5% G-polymer in water solution including 0.4 milligrams/milliliters of a Food, Drug & Cosmetic blue dye. G-polymer is a vinyl alcohol polymer that is water soluble and non-gel-forming. With regard to the third sample, the hydrophilic reservoir layer was loaded with 500 microliters of a 5% ExpertGel 230 polymer in water solution including 0.4 milligrams/milliliters of a Food, Drug & Cosmetic blue dye. Visual observation suggested that the compositions in all three samples remained largely in the hydrophilic reservoir layers of each sample. Each sample was then wiped across the palm of a human hand five times. The skin area contacted by the first sample had very weak blue color; the skin area contacted by the second sample had a medium blue color; and the skin area contacted by the third sample had the strongest blue color. The strength of the blue color is representative of the amount of composition transferable to the skin when the composite structure of the invention is used to apply an active ingredient.

In a second experiment, a composite structure was formed of a hydrophobic support layer and a hydrophilic reservoir layer. The hydrophobic support layer was formed of a meltblown melamine fiber web having a basis weight of about 20 grams per square meter and the hydrophilic reservoir layer was formed of VIVA brand paper towel. The two-layered composite structure was formed by laminating the layers together with a multipurpose spray adhesive, such as 3M SUPER 77 spray adhesive. The composite structure was cut into three (3) samples each having dimensions of 2 inches by 2 inches. With regard to the first sample, the hydrophilic reservoir layer was loaded with 500 microliters of water including 0.4 milligrams/milliliters of a Food, Drug & Cosmetic blue dye. With regard to the second sample, the hydrophilic reservoir layer was loaded with 500 microliters of a 5% G-polymer in water solution including 0.4 milligrams/milliliters of a Food, Drug & Cosmetic blue dye. With regard to the third sample, the hydrophilic reservoir layer was loaded with 500 microliters of a 5% ExpertGel 230 polymer in water solution including 0.4 milligrams/milliliters of a Food, Drug & Cosmetic blue dye. Visual observation suggested that the compositions in all three samples remained largely in the hydrophilic reservoir layers of each sample. Each sample was then wiped across the palm of a human hand five times. The skin area contacted by the first sample had very weak blue color; the skin area contacted by the second sample had a medium blue color; and the skin area contacted by the third sample had the strongest blue color. The strength of the blue color is representative of the amount of composition transferable to the skin when the composite structure of the invention is used to apply an active ingredient.

In a third experiment, a composite structure was formed of a hydrophobic support layer and a hydrophilic reservoir layer. The hydrophobic support layer was formed of weighing paper and the hydrophilic reservoir layer was formed of a pulp-containing coform material. The two-layered composite structure was formed by laminating the layers together with 3M SUPER 77 spray adhesive. The composite structure was cut into three (3) samples each having dimensions of 2 inches by 2 inches. With regard to the first sample, the hydrophilic reservoir layer was loaded with 500 microliters of water including 0.4 milligrams/milliliters of a Food, Drug & Cosmetic blue dye. With regard to the second sample, the hydrophilic reservoir layer was loaded with 500 microliters of a 5% G-polymer in water solution including 0.4 milligrams/milliliters of a Food, Drug & Cosmetic blue dye. G-polymer is a vinyl alcohol polymer that is water soluble and non-gel-forming. With regard to the third sample, the hydrophilic reservoir layer was loaded with 500 microliters of a 5% ExpertGel 230 polymer in water solution including 0.4 milligrams/milliliters of a Food, Drug & Cosmetic blue dye. Visual observation suggested that the compositions in all three samples remained largely in the hydrophilic reservoir layers of each sample. Each sample was then wiped across the palm of a human hand five times. The skin area contacted by the first sample had very weak blue color; the skin area contacted by the second sample had a medium blue color; and the skin area contacted by the third sample had the strongest blue color. The strength of the blue color is representative of the amount of composition transferable to the skin when the composite structure of the invention is used to apply an active ingredient.

Each of the three experiments representatively illustrates how composite structures of the invention improve the transfer of composition to the skin through the use of a phase change polymer.

What is claimed is:

1. A composite structure comprising a hydrophobic support layer and a hydrophilic reservoir layer wherein the hydrophilic reservoir layer includes a composition that changes phase at a phase change temperature that is between 30-35 degrees Celsius and is liquid at temperatures below the phase change temperature and that is a hydrogel at temperatures above the phase change temperature, wherein the composite structure is configured to transfer the composition from the hydrophilic reservoir layer to a target surface when the hydrophilic reservoir layer comes into contact with the target surface.

2. The composite structure of claim 1, wherein the hydrophobic support layer is formed of one or more of urea formaldehyde fibers, polyester resin fibers, epoxy resin fibers, melamine formaldehyde fibers, polycarbonate fibers, silicone particles and cellulose fibers coated with a hydrophobic coating.

3. The composite structure of claim 1, wherein the hydrophobic support layer has a thermal conductivity that is 5 to 30 times less, in watts per meter kelvin, than water.

4. The composite structure of claim 1, wherein the hydrophilic reservoir layer is formed of cellulose fibers.

5. The composite structure of claim 4, wherein the hydrophilic reservoir layer is further formed of 50% or less, by total fiber composition, of thermoplastic fibers.

6. The composite structure of claim 1, wherein the composition includes a phase change polymer selected from poly(N-isopropylacrylamide); poly(hydroxypropyl methacrylamide); triblock copolymers of polyethylene glycol and poly(hydroxypropyl methacrylamide); triblock copolymers of methyl acrylated poly(N-2-hydroxypropyl) methacrylamide lactate and polyethylene glycol; poloxamers; chitosan and glycerol phosphate disodium; and chitosan-PEG copolymers.

7. The composite structure of claim 1, wherein the composition includes an active ingredient selected from an antioxidant, a skin moisturizer, Vitamin E and Vitamin C.

8. The composite structure of claim 1, wherein a ratio of a relative thickness of the hydrophobic support layer to the hydrophilic reservoir layer is from 1:1 to 1:5.

9. The composite structure of claim 1, wherein the hydrophobic support layer and the hydrophilic reservoir layer are laminated together.

10. The composite structure of claim 1, wherein the hydrophobic support layer and the hydrophilic reservoir layer are entangled together.

11. The composite structure of claim 1, wherein the hydrophilic reservoir layer includes fibers and further wherein a ratio of a relative weight of the fibers to the composition is from 1:1 to 1:3.

12. The composite structure of claim 1, wherein the target surface is a user's skin.

* * * * *